(12) United States Patent
McCune et al.

(10) Patent No.: US 8,512,267 B2
(45) Date of Patent: Aug. 20, 2013

(54) OVER-MOLDED FLEXIBLE KNEE BRACE

(75) Inventors: Robert J. McCune, Escalon, CA (US);
John M. Petlansky, Tracy, CA (US);
Jeffrey D. Leonard, Livermore, CA (US)

(73) Assignee: Top Shelf Manufacturing, LLC, Tracy, CA (US)

( * ) Notice: Subject to any disclaimer, the term of this patent is extended or adjusted under 35 U.S.C. 154(b) by 84 days.

(21) Appl. No.: 13/043,196

(22) Filed: Mar. 8, 2011

(65) Prior Publication Data

US 2011/0218470 A1    Sep. 8, 2011

Related U.S. Application Data

(60) Provisional application No. 61/311,650, filed on Mar. 8, 2010.

(51) Int. Cl.
*A61F 5/00* (2006.01)

(52) U.S. Cl.
USPC .................................. 602/16; 602/23; 602/26

(58) Field of Classification Search
USPC .......................... 602/16, 23, 26–27; 128/882
See application file for complete search history.

(56) References Cited

U.S. PATENT DOCUMENTS

| | | | | |
|---|---|---|---|---|
| 5,403,002 A | * | 4/1995 | Brunty | 473/438 |
| 5,662,596 A | * | 9/1997 | Young | 602/26 |
| 6,527,733 B1 | * | 3/2003 | Ceriani et al. | 602/16 |
| 6,953,442 B2 | * | 10/2005 | Yamasaki et al. | 602/22 |
| 7,306,572 B2 | * | 12/2007 | Ceriani et al. | 602/16 |
| 7,311,687 B2 | * | 12/2007 | Hoffmeier et al. | 602/26 |

* cited by examiner

*Primary Examiner* — Michael A. Brown
(74) *Attorney, Agent, or Firm* — Dickstein Shapiro LLP

(57) ABSTRACT

A fitted hinge brace for supporting a joint that employs a flexible over-molding over hinge arms. The over-molded hinge brace dynamically conforms to the shape of the wearer in real-time, working with the wearer's body to provide comfortable support. The hinge brace includes first and second cuffs with flexible over-molding formed over medial and lateral hinges. The medial and lateral hinges each include a hinge arm and a hinge plate with geared portion. The geared portions of the medial hinge plate of the first cuff fit between the geared portions of the medial hinge plate of the second cuff, and the geared portions of the lateral hinge plate of the first cuff fit between the geared portions of the lateral hinge plate of the second cuff.

15 Claims, 3 Drawing Sheets

Lateral View

OVER-MOLDED FLEXIBLE KNEE BRACE

This application claims the benefit of U.S. Provisional Application No. 61/311,650, filed Mar. 8, 2010.

BACKGROUND OF THE INVENTION

1. Field of the Invention

The present invention is directed to a hinge brace used to support a joint.

2. Description of the Related Art

Prior knee braces provide support for the leg and knee joint using a rigid or semi-rigid frame and hinge attached to the leg of a wearer. Leg and knee support in such braces is provided by the rigidity of the frame. Prior knee braces work against the body of the wearer to provide support.

Rigid frame knee braces evolved to provide a more-fitted shape for the wearer. However, the shaping of those knee braces cannot adapt to the shape of the patient's leg in real time. For example, during movement, the shape of the leg changes, resulting in an imperfect fit. Additionally, post injury or post operative joints and the surrounding areas swell and contract, resulting in different leg shapes. Furthermore, support for the leg by these types of braces is still provided by the rigidity of the frame.

Rigid knee braces are also uncomfortable. The inherent hardness of those, braces makes lengthy wearing and use difficult and uncomfortable for the wearer. Accordingly, it would be desirable to provide a knee brace that is more flexible and comfortable than the rigid knee braces of the prior art.

SUMMARY OF THE INVENTION

The present invention advantageously overcomes the above-noted deficiencies of the prior art, and provides a comfortable, fitted hinge brace for supporting a joint by employing a flexible over-molding over hinge arms. Rather than working against the body, like prior braces, the over-molded hinge brace dynamically conforms to the shape of the wearer in real-time, working with the wearer's body to provide support. The components of the present invention provide stability for a joint by working as a system. Furthermore, the over-molded hinge brace is more comfortable to wear, as it does not have a rigid frame which can press uncomfortably into a wearer's body.

More specifically, the hinge brace of the present invention includes first and second cuffs with flexible over-molding formed over medial and lateral hinges. The medial and lateral hinges each include a hinge arm and a hinge plate with geared portion. The geared portions of the medial hinge plate of the first cuff fit between the geared portions of the medial hinge plate of the second cuff, and the geared portions of the lateral hinge plate of the first cuff fit between the geared portions of the lateral hinge plate of the second cuff.

These and other features and advantages of the invention will be more apparent from the following detailed description that is provided in connection with the accompanying drawings and illustrated exemplary embodiments of the invention.

DETAILED DESCRIPTION OF THE PREFERRED EMBODIMENT

Figure 1:
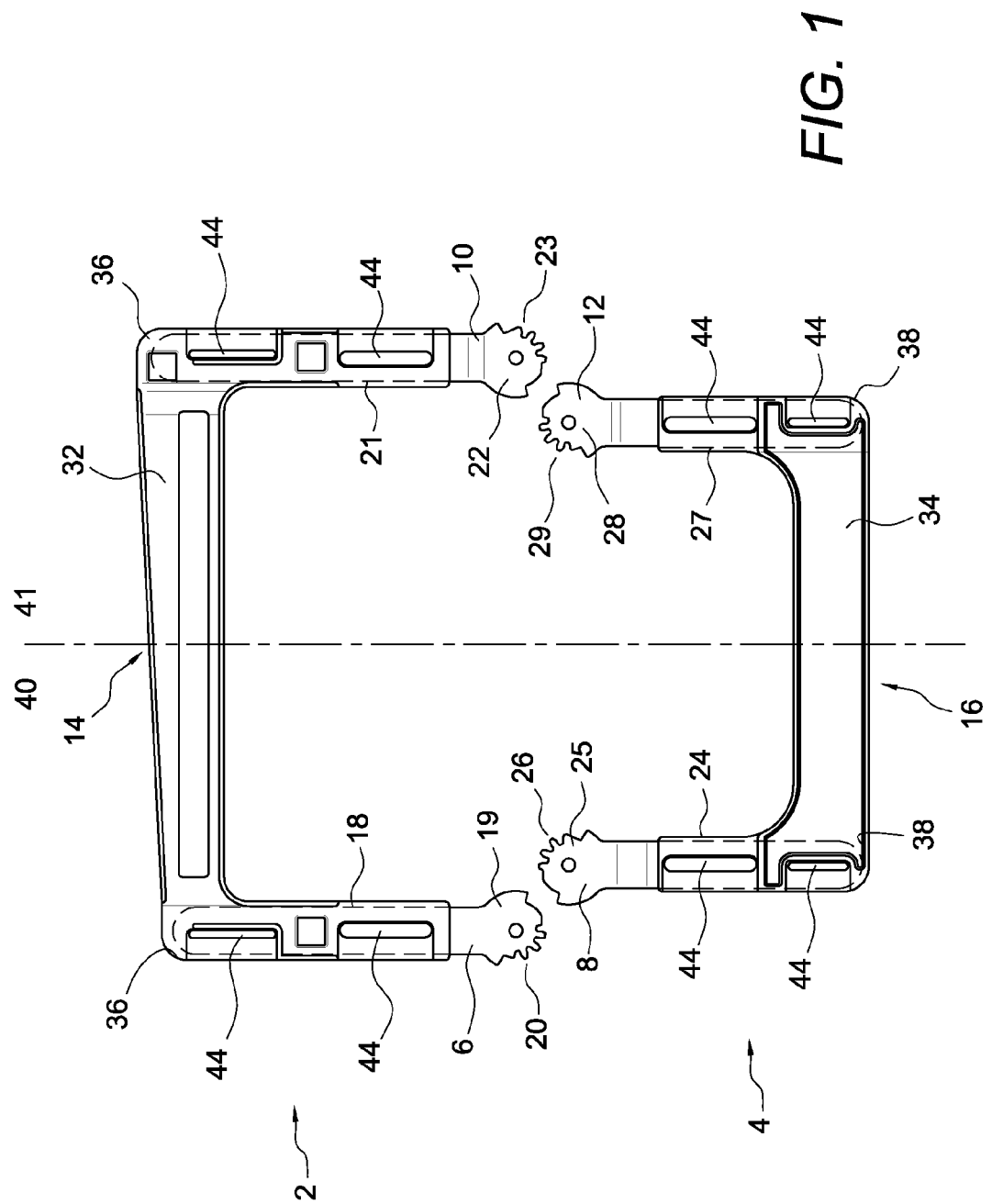
FIG. 1 shows an upper portion and a lower portion of a right-leg hinge brace.

FIG. 1 shows an upper portion 2 and a lower portion 4 components of the hinge brace 1 for the right leg. The upper portion 2 forms the upper cuff 32 and the lower portion 4 forms the lower cuff 34. The upper portion 2 and lower portion 4 have a medial side 40 and a lateral side 41. The upper portion 2 comprises an upper flexible over-molding 14 formed over an upper medial hinge 6 and an upper lateral hinge 10. The lower portion 4 comprises a lower flexible over-molding 16 formed over a lower medial hinge 8 and a lower lateral hinge 12.

Upper medial hinge 6 is formed of a rigid material and comprises an upper medial hinge arm 18 represented by dashed lines, an upper medial hinge plate 19, and upper medial hinge plate geared portions 20. Similarly, upper lateral hinge 10 is formed of a rigid material and comprises an upper lateral hinge arm 21, represented by dashed lines, an upper lateral hinge plate 22, and upper lateral hinge plate geared portions 23. Similarly, lower medial hinge 8 is formed of a rigid material and comprises a lower medial hinge arm 24, represented by dashed lines, a lower medial hinge plate 25, and lower medial hinge plate geared portions 26. Similarly, lower lateral hinge 12 is formed of a rigid material and comprises a lower lateral hinge arm 27, represented by dashed lines, a lower lateral hinge plate 28, and a lower lateral hinge plate geared portions 29. As shown, hinge arms 18, 21, 24, and 27 are over-molded by upper and lower flexible over-molding 14 and 16.

The over-molded upper portion 14 is a continuous material, comprising an upper-cuff 32 and hinge arm over-molding 36. The over-molded upper portion 14 is formed of a flexible material. As can be seen, the upper-cuff 32 tapers from the lateral-side 41 of the hinge brace to the medial side 40 of the hinge brace. The tapering assists in fitting the upper portion 2 to the thigh of the wearer. Similarly, the over-molded lower portion 16 is a continuous material, comprising a lower-cuff 34, and hinge arm over molding 38. The over-molded lower portion 16 is formed of a flexible material. The flexible material is preferably formed of urethane and can be an ethyl or ester based material.

Upper portion 14 and lower portion 16 include strap points 44, where straps may be connected. The straps can be a hook and loop type material (e.g., Velcro™) to secure and fit the hinge brace to the leg of the wearer, as well as provide support for the leg.

Figure 2:
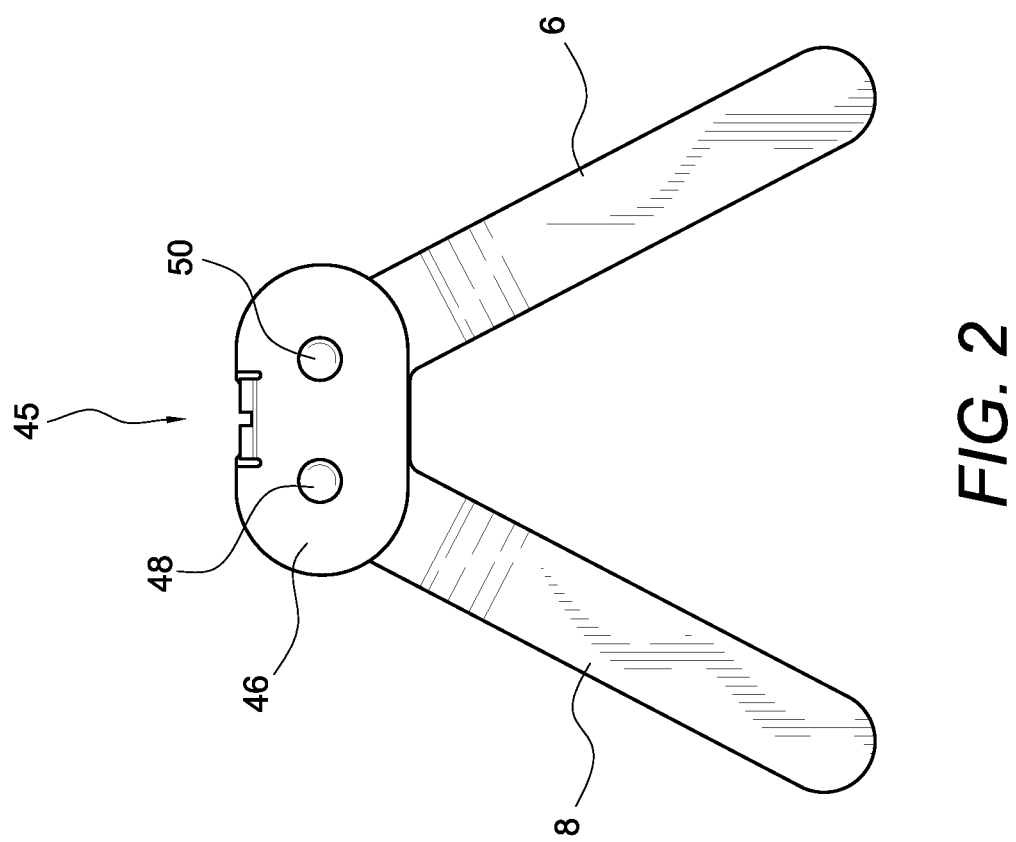
FIG. 2 shows a hinge that can be used in the hinge brace.

FIG. 2 shows a typical connection between hinge portions to create a hinge 45. For example an upper medial hinge 6 and a lower medial hinge 8 can attach to a top hub 50 and a bottom hub 48, respectively, between a top plate 46 and a bottom plate (not shown). The upper medial hinge 6 geared portions 20 fit between lower medial hinge 8 geared portions 26. This provides a simple hinge action between the upper medial hinge arm 18 and lower medial hinge arm 24. The range of motion for the hinge is limited by the arc of geared portions 20 and 26. A similar arrangement can be used between upper lateral hinge 10 and lower lateral hinge 12.

Figure 3:
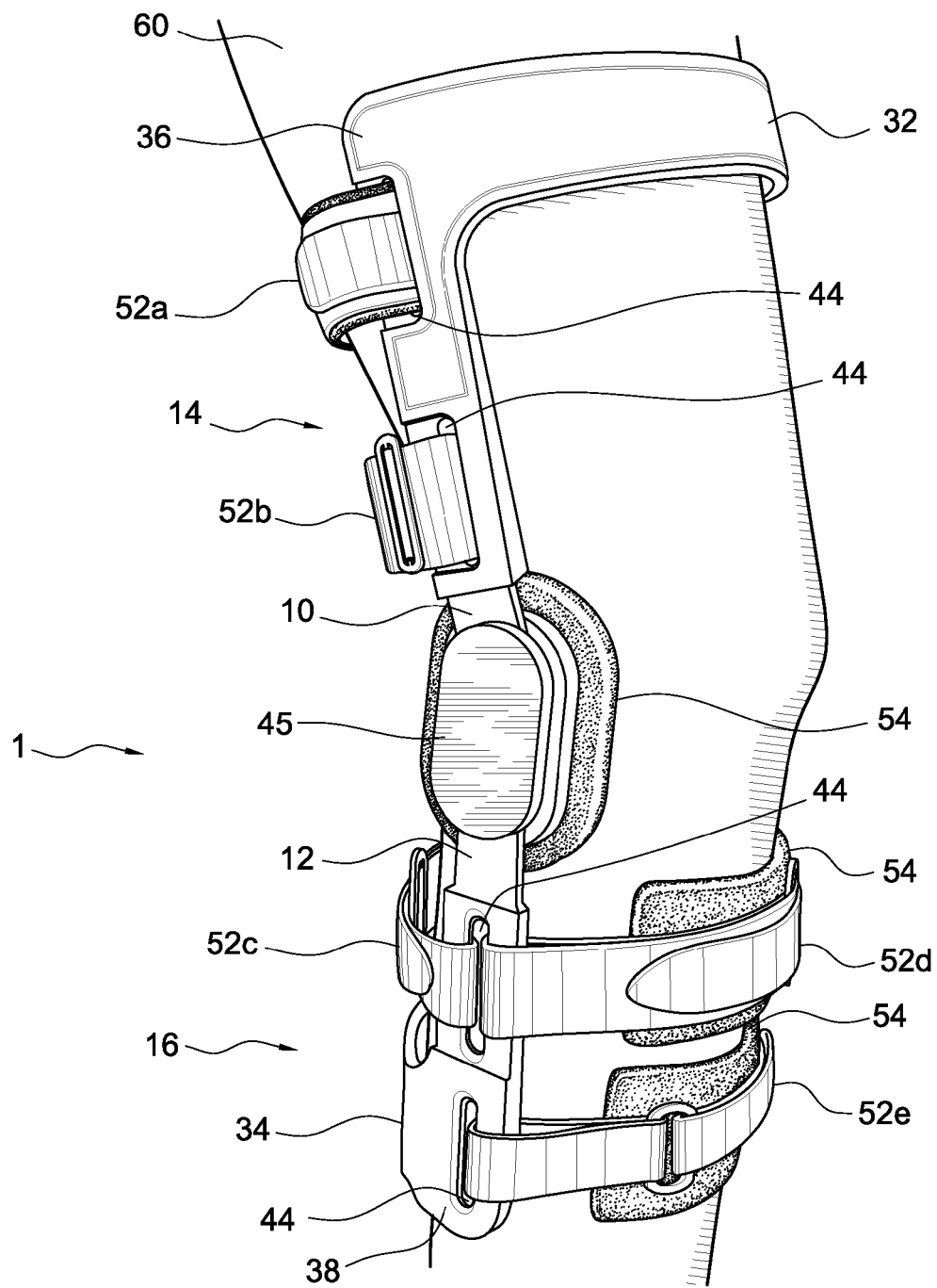
FIG. 3 shows a lateral view of a hinge brace on a right leg.

FIG. 3 shows the hinge brace 1 attached to a wearer's right leg 60 and depicts the lateral side of the leg. The hinge brace 1 comprises an upper portion 14, a lower portion 16, and a hinge 45, similar to the arrangement described above. The hinge brace 1 also comprises straps 52a-e, attached at strap points 44, for attaching and fitting the hinge brace to the leg of the wearer. The hinge brace may also comprise padding 54, to increase the wearer's comfort.

The hinge brace 1 is placed around the leg 60 of the wearer. The upper portion 14 of the hinge brace 1 is positioned such that the upper cuff 32 contacts the front of the thigh. The lower portion 16 of the hinge brace 1 is positioned such that the lower cuff 34 contacts the back calf area. Once the hinge brace 1 is positioned, it is attached and fitted to the leg 60 of the wearer by straps 52a-e. By using a flexible over-molding, the upper cuff 36 and lower cuff 34 can form to the shape of the wearer's leg when straps 52a-e are tightened. The flexible over molding allows the hinge brace 1 to mold and conform to the shape of the body, allowing the hinge brace 1 to utilize the wearer's leg 60 to help provide stability. Furthermore, the flexible over molding dynamically changes shape in real time as the shape of the leg 11 changes when the leg 11 is active or if the leg 11 swells or contracts.

Unlike prior rigid braces, the hinge brace 1 does not provide stability through a rigid frame, but rather works with the wearer's leg and body to provide support. The hinge brace 1 provides stability and support through the various components operating together. For example, the straps 52a-e help provide support. It is important that the over-molding of the upper portion 14 upper cuff 32 and lower portion 16 lower cuff 34 be flexible enough to dynamically change shape to fit the wearer's leg in real time. While the material must be flexible enough to dynamically change shape, it must also be stiff enough to provide support. Furthermore, different size wearers will require different flexibility in the over-molding. The flexibility of the over-molding is determined by the type of material used to form the over-molding, the thickness of the over-molding, or the shape of the over-molding. The flexibility of the over-molding can also be adjusted using inserts placed within the over molding.

While the exemplary embodiment is for a knee brace, the over-molded hinge brace can easily be adapted for use on other joints. Furthermore, the over-molded hinge brace is described for use with a knee brace to support a joint, however, the invention of the over-molded hinge brace can be used with a brace that provides telescopic expansion or a brace that limits the range of motion for a joint. The above description and drawings are only illustrative of certain preferred versions which achieve the objects, features and advantages of the present invention. It is not intended that the present invention be limited to these versions.

We claim:

1. A hinge brace comprising:
a first cuff with a first flexible over-molding formed over a portion of a first medial hinge and a first lateral hinge, wherein the first flexible over-molding is formed of a continuous, flexible material, and the first medial hinge comprises: a first medial hinge arm and a first medial hinge plate with geared portions, and the first lateral hinge comprises: a first lateral hinge arm and a first lateral hinge plate with geared portions; and
a second cuff with a second flexible over-molding formed over a portion of a second medial hinge and a second lateral hinge, wherein the second flexible over-molding is formed of a continuous, flexible material, and the second medial hinge comprises: a second medial hinge arm and a second medial hinge plate with geared portions, and the second lateral hinge comprises: a second lateral hinge arm and a second lateral hinge plate with geared portions,
wherein the geared portions of the first medial hinge plate fit between the geared portions of the second medial hinge plate, and the geared portions of the first lateral hinge plate fit between the geared portions of the second lateral hinge plate.

2. The hinge brace of claim 1, wherein the first cuff tapers in a direction from the first lateral hinge to the first medial hinge.

3. The hinge brace of claim 1, wherein the flexible material is selected from the group consisting of urethane, an ethyl-based material and an ester-based material.

4. The hinge brace of claim 1, wherein the first medial hinge, the first lateral hinge, the second medial hinge, and the second lateral hinge are formed of a rigid material.

5. The hinge brace of claim 1, wherein the first medial hinge arm, the first lateral hinge arm, the second medial hinge arm, and the second lateral hinge arm comprise strap points.

6. The hinge brace of claim 5, wherein straps are connected to the strap points.

7. A hinge brace comprising:
a first cuff with a first flexible over-molding formed over a portion of a first medial hinge and a first lateral hinge, wherein the first medial hinge comprises: a first medial hinge arm and a first medial hinge plate with geared portions, and the first lateral hinge comprises: a first lateral hinge arm and a first lateral hinge plate with geared portions; and
a second cuff with a second flexible over-molding formed over a portion of a second medial hinge and a second lateral hinge, wherein the second medial hinge comprises: a second medial hinge arm and a second medial hinge plate with geared portions, and the second lateral hinge comprises: a second lateral hinge arm and a second lateral hinge plate with geared portions,
wherein the geared portions of the first medial hinge plate fit between the geared portions of the second medial hinge plate, and the geared portions of the first lateral hinge plate fit between the geared portions of the second lateral hinge plate, and
wherein the first medial hinge and the second medial hinge are attached to a first top hub and a first bottom hub between a first top hub plate and a first bottom hub plate, and the first lateral hinge and the second lateral hinge are attached to a second top hub and a second bottom hub between a second top hub plate and a second bottom hub plate.

8. The hinge brace of claim 7, further comprising padding.

9. The hinge brace of claim 7, wherein the first flexible over-molding and the second flexible over-molding are capable of conforming to the shape of a body part.

10. The hinge brace of claim 7, wherein the first cuff tapers in a direction from the first lateral hinge to the first medial hinge.

11. The hinge brace of claim 7, wherein the first flexible over-molding and the second flexible over-molding are formed of a continuous, flexible material.

12. The hinge brace of claim 7, wherein the first medial hinge, the first lateral hinge, the second medial hinge, and the second lateral hinge are formed of a rigid material.

13. The hinge brace of claim 7, wherein the first medial hinge arm, the first lateral hinge arm, the second medial hinge arm, and the second lateral hinge arm comprise strap points.

14. The hinge brace of claim 13, wherein straps are connected to the strap points.

15. The hinge brace of claim 14, wherein the straps are made of Velcro material.

* * * * *